(12) United States Patent
Tuunanen

(10) Patent No.: US 9,568,403 B2
(45) Date of Patent: Feb. 14, 2017

(54) PARTICLE PROCESSING

(75) Inventor: Jukka Tuunanen, Helsinki (FI)

(73) Assignee: THERMO FISHER SCIENTIFIC OY, Vantaa (FI)

( * ) Notice: Subject to any disclaimer, the term of this patent is extended or adjusted under 35 U.S.C. 154(b) by 677 days.

(21) Appl. No.: 14/001,301

(22) PCT Filed: Feb. 22, 2012

(86) PCT No.: PCT/FI2012/050173
§ 371 (c)(1),
(2), (4) Date: Nov. 4, 2013

(87) PCT Pub. No.: WO2012/113986
PCT Pub. Date: Aug. 30, 2012

(65) Prior Publication Data
US 2014/0099658 A1  Apr. 10, 2014

(30) Foreign Application Priority Data
Feb. 23, 2011  (FI) ....................... 20115175

(51) Int. Cl.
*G01N 1/40*   (2006.01)
*G01N 33/543*   (2006.01)
(Continued)

(52) U.S. Cl.
CPC ............. *G01N 1/4077* (2013.01); *B03C 1/01* (2013.01); *B03C 1/0332* (2013.01); *B03C 1/284* (2013.01);
(Continued)

(58) Field of Classification Search
CPC ............. G01N 1/4077; G01N 33/5434; G01N 35/0098; B03C 1/288; B03C 1/286; B03C 1/0332; B03C 1/01; B03C 1/284; B03C 2201/18; B03C 2201/26
See application file for complete search history.

(56) References Cited

U.S. PATENT DOCUMENTS 4,649,116 A * 3/1987 Daty ................. B03C 1/284
                                                    210/222
6,596,162 B2 * 7/2003 Tuunanen ........... B03C 1/284
                                                    210/222
(Continued)

FOREIGN PATENT DOCUMENTS

WO   WO 02/073159     9/2002
WO   WO 2009/076560   6/2009

OTHER PUBLICATIONS

Written Opinion for PCT/Fi2012/050173, dated Jun. 13, 2012.*
International Search Report for PCT/FI2012/050173, mailed Jun. 13, 2012.

*Primary Examiner* — David A Reifsnyder
(74) *Attorney, Agent, or Firm* — Nixon & Vanderhye P.C.

(57) ABSTRACT

The invention concerns a method for processing magnetic particles, which selectively interact with a substance present in a liquid medium. The particles are collected with a probe (2) comprising a hollow shield (4) and a probe magnet (3) moveable up and down. The lower end of the probe with the collected particles is placed on a release location (7) of a plate (6), below which release location there is a release magnet (8). The surface of the release location is dry or has a liquid film or a drop on it. In accordance with the invention, very high concentration ratios can be achieved.

10 Claims, 1 Drawing Sheet

Figure 1:
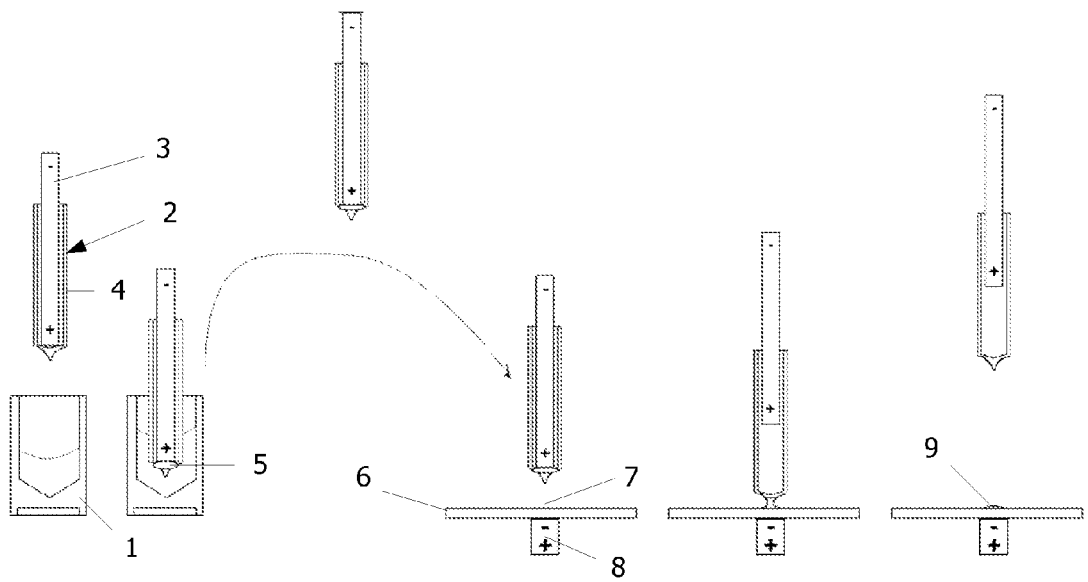

(51) Int. Cl.
*G01N 35/00* (2006.01)
*B03C 1/033* (2006.01)
*B03C 1/01* (2006.01)
*B03C 1/28* (2006.01)

(52) U.S. Cl.
CPC ............... *B03C 1/286* (2013.01); *B03C 1/288* (2013.01); *G01N 33/5434* (2013.01); *B03C 2201/18* (2013.01); *B03C 2201/26* (2013.01); *G01N 35/0098* (2013.01)

(56) References Cited

U.S. PATENT DOCUMENTS

| | | | |
|---|---|---|---|
| 7,622,046 | B2 | 11/2009 | Rundt et al. |
| 7,632,405 | B2 | 12/2009 | Siddiqi |
| 2002/0086443 | A1 | 7/2002 | Bamdad |
| 2003/0040129 | A1 | 2/2003 | Shah |
| 2006/0269385 | A1 | 11/2006 | Zobel et al. |
| 2008/0308500 | A1 | 12/2008 | Brassard |

* cited by examiner

PARTICLE PROCESSING

This application is the U.S. national phase of International Application No. PCT/FI2012/050173, filed 22 Feb. 2012, which designated the U.S. and claims priority to FI Application No. 20115175, filed 23 Feb. 2011, the entire contents of each of which are hereby incorporated by reference.

TECHNICAL FIELD

The invention relates to laboratory technology in which magnetic particles are used to separate substances from a liquid medium. The invention concerns especially the release of particles from a magnetic probe to which they have been collected. The invention can be used especially for separating biological materials.

TECHNICAL BACKGROUND

Magnetic particles can be used for separating a specific substance from a liquid medium. Such particles are coated with a specific reagent interacting with the substance or the substance intrinsically adheres to the surface of the particles. The particles together with the substance attached to them are separated from the liquid. This has conventionally been done by removing the liquid. Nowadays also magnetic separating probes are used. Such a probe comprises a magnet moveable up and down within an elongate covering shield. The particles are collected on the surface of the shield keeping the magnet in its lower position. The probe is then transferred to another liquid, and the magnet is moved to its upper position, whereby the particles are released. Such a process has been described e.g. in U.S. Pat. No. 6,040,192 and U.S. Pat. No. 6,447,729.

The concentration ratio, i.e. the ratio of the start volume to the end volume, is preferably maximized so that collected particles can be further processed as effectively as possible. The start volume is often relatively big (e.g. >1000 µl), and the concentration of the substance to be collected may be very low. The collected particles may be released into a very small liquid volume by utilizing liquid adhesion, whereby the particles are washed off by a small liquid amount that wets the surface on which the particles have been collected. With a suitable design of the probe and vessel, very small release volumes (e.g. 5-10 µl) may be achieved. Such processes have been described e.g. in U.S. Pat. No. 6,207,463, U.S. Pat. No. 6,448,092, and U.S. Pat. No. 6,596,162.

WO 99/40444, US 2006269385, and WO 2009076560 describe processes, in which magnets are additionally used under the receiving vessels in order to facilitate the release of particles from the probes into the liquid.

SUMMARY OF THE INVENTION

Now an invention according to the claims has been made.

According to the invention, magnetic particles are released from a probe on a plate with the help of a magnet placed below the surface of the plate. The surface of the plate is dry or it has a liquid film or a drop on it.

In accordance with the invention, very high concentration ratios can be achieved.

The plate may be e.g. a microscope slide, a growing substrate, or the bottom of a container.

DRAWINGS

The enclosed drawings form a part of the written description relating to some exemplifying embodiments of the invention.

Figure 2:
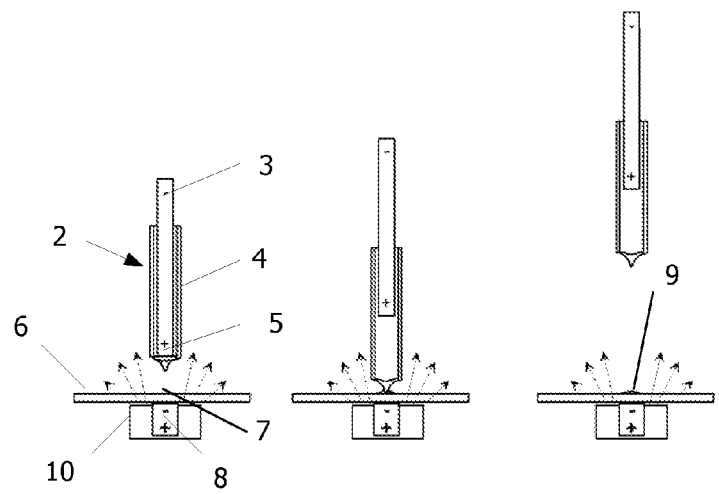

FIG. 1 shows steps of a separation process, and
FIG. 2 shows a modification of the process.

DETAILED DESCRIPTION OF THE INVENTION

The size of the magnetic particles used in the method is usually 0.5-10 µm, typically 1-5 µm. A large variety of such particles are commercially available. The particles are coated with an affinity reagent for the substance to be separated, or the surface intrinsically interacts with the substance. For example a silica surface may interact with nucleic acids without specific coating. The sample is typically a biological sample, and the substance to be separated may for example consist of cells (e.g. bacteria or cancer cells), proteins (e.g. antigens or antibodies), enzymes, or nucleic acids.

The volume of the sample from which the particles are collected is typically 20-1000 µl, but also essentially larger or smaller volumes have sometimes to be used.

The probe that is used to collect the particles comprises a hollow shield with a closed lower end and inside it a magnet moveable up and down. When the particles are collected, the magnet is kept in its lower position, whereby the particles attach to the lower end of the shield. When the particles are released, the magnet is lifted to its upper position, in which the magnet no longer holds the particles attached on the shield. However, the particles still tend to remain on the shield by the adhesion of the small amount of liquid transferred together with the particles.

The magnet is preferably a permanent magnet. The magnet is preferably long so that the particles are attached as a concentrated spot or ring on the end of the shield. Most preferably, the magnet is so long that the upper pole of the magnet is kept above the surface of the liquid, see e.g. U.S. Pat. No. 6,207,463 and U.S. Pat. No. 6,448,092. When the particles are collected from a large liquid volume (e.g. up to 50 ml), it may be preferable to concentrate the particles first on the side wall or bottom of the vessel, see e.g. U.S. Pat. No. 6,020,211. When the particles are collected from a very small liquid volume (e.g. 5-10 µl), it may be preferable to use a vessel having a small recess on the bottom, see e.g. U.S. Pat. No. 6,596,162.

The particles are released from the shield on a release location on the surface of a plate. The particles are attracted from the shield towards the plate by means of a release magnet placed under the release location. On the surface of the shield there is together with the particles a thin liquid film. This helps in removing the particles from the shield.

The release magnet may be a vertically placed magnet, preferably a rod magnet. When the probe magnet is also vertical, the opposite poles of the magnets are preferably placed against each other so that the probe is automatically correctly orientated towards the release location. If this is desired, the magnet in the shield must be still kept at a sufficiently low position when the probe is brought on the plate. When there is a plurality of release locations on the release plate, there may be release magnet below each release location. Alternatively there may a single or a group of magnets and the plate or the magnets are removed in the release step so that a magnet is brought under a release location when needed.

The release location may also be in some way marked in order to facilitate correct placing of the probe. When the plate is sufficiently transparent, the release location may be surrounded by a light source below the plate. The release location may be marked also by printing or like.

The surface of the release location may be dry. The small amount of liquid (typically much less than 1 µl) transferred together with the particles is easily evaporated, whereby a fully dry sample is obtained. The particles may be released e.g. on a microscope slide, when a microscopic investigation is to be carried out. The particles may be released also on a growing substrate (e.g. in a Petri dish), when possible microbe (e.g. bacteria or fungi) growth is to be monitored. The particles may be released also on the bottom of a container, e.g. a storage container. The plate may comprise several release locations. Further, the particles may be released on a filter material.

The release location may also have a liquid film or a drop on it. A liquid film is a thin layer (less than about 0.3 mm) held evenly on a surface by adhesion. E.g., the surface of a growing substrate may be wet and thus it can be said to have a thin liquid film on it. A liquid drop on the release location may help the complete removal of the particles. A drop is formed from a small liquid volume (less than about 0.2 µl) held together by surface tension. The liquid is after the release then evaporated away, if necessary.

The release location may be surrounded by a coating which is more repellent to the liquid than the surface of the release location is.

The shape of the release magnet determines the shape of particle spot obtained. A large diameter rod magnet is more efficient, but correspondingly forms a wider spot. If a more point-like spot is desired, a thinner rod magnet is used or there is an additional ferromagnetic piece to modify the magnetic field. The release magnet is preferably a permanent magnet, but also an electric magnet may be used.

The release magnet may also be comprised of several magnets. They are preferably placed so that their similar poles are placed against each other. Thereby a very sharp field gradient can be achieved and the particles can thus be released exactly on a very small area.

It is also possible to use multi-magnet arrays, whereby a separating apparatus comprising several probes in a matrix form is used, see e.g. WO 2005/044460. Then there is under the receiving plate also a plurality of release magnets in the corresponding matrix form. Particles can also be brought from discrete sources collecting from one source at a time to form a set particle spots.

In accordance with the invention, very high concentration ratios can be achieved. Especially when the particles are released on a dry surface, only the very small amount of liquid transferred with the particles is present.

The invention may be applied in different manual or automatic apparatus constructions.

A special advantage is achieved when the particles are released on a slide for microscopic research. By using magnetic particles, a very low concentration of the target substance can be enriched to aid microscopic study. When the particles are released on a glass slide, free particles (i.e. particles without attached substance) are moving faster toward the glass surface than particles which have attached the substance (e.g. bacteria) because of lower viscous friction of free particles. Free particles will thus sediment below. This makes top reading microscopy more efficient. It is also possible that e.g. cells can rotate on the glass plate so that most of attached particles will reside underneath the cells and this further will help top reading microscopic study.

Some embodiments of the invention are further exemplified in the following.

In the process of FIG. 1, a vessel 1 contains a liquid sample from which a desired substance is to be separated. Therefore magnetic micro particles selectively interacting with the substance have been suspended with the sample. The particles interact with the substance, and the substance is thereby fixed on the surface of the particles. Thereafter a magnetic probe 2 is introduced into the vessel in order to collect the particles. The probe comprises an elongate permanent magnet 3 covered by a hollow shield 4. The magnet is moveable up and down in the shield, and the particles are collected keeping the magnet in its lower position. The upper end of the magnet extends well above the liquid surface in the vessel. The lower end of the shield has tapering concave surface with a sharp tip. The particles collect as a ring 5 on the concave surface area. When collecting the particles, the probe is moved a few times slowly up and down.

After the particles have been collected to the probe 2, the probe is lifted out of the vessel 1 keeping the magnet 3 still in its lower position, whereby the particles keep reliably attached to the probe. In practice the particles would keep attached to the probe after it has been lifted from the vessel even if the magnet were lifted from the lower position. After removal from the vessel, the particles are usually washed in at least one step, and preferably in several steps. The washing is preferably carried out so that the end of the probe is placed in a washing liquid and the magnet lifted, whereby the particles are released into the liquid. After washing, the particles are again collected by the probe. A small amount of liquid is adhered to the surfaces of the particles, i.e. the particles are wet. The probe is moved and contacted perpendicularly with a horizontal plate 6 at a release location 7. Below the release location there is a release magnet 8 comprising a magnetic rod aligned with the probe magnet 3 so that opposite poles are towards each other. The probe magnet is now moved upwards, whereby by the release magnet attracts the particles as a concentrated spot 9 on the release location.

The plate 6 may be e.g. a microscope glass slide or the growing substrate of a Petri dish.

In the embodiment of FIG. 2, the release location is surrounded by ring-like LED light source 10 to show exactly the release location and thereby facilitating positioning of the probe.

The invention claimed is:
1. A method comprising:
(a) providing a probe which comprises a hollow shield having a lower end portion with a closed bottom end and a probe magnet moveable up and down in the shield such that the probe magnet has an upper position and a lower position;
(b) providing magnetic particles which are arranged to selectively interact with a target substance;
(c) providing a liquid medium containing the target substance in a vessel;
(d) introducing the magnetic particles into the liquid medium such that the magnetic particles selectively interact with the target substance so that the target substance is fixed to the magnetic particles:
(e) introducing the probe into the liquid medium by keeping the probe magnet in the lower position such that at least a part of the magnetic particles are attached on the lower end portion of the shield;
(f) lifting the probe together with the magnetic articles attached to the lower end portion of the shield from the liquid medium;
(g) placing the lower end portion of the shield on a release location of a plate having a release magnet located below the release location to attract the magnetic particles, wherein a surface of the release location is either dry, has as a liquid film or a drop of liquid smaller than 0.2 μl thereon; and (h) removing the magnetic particles from the lower end portion of the shield on the release location by lifting the probe magnet from the lower position to the upper position.

2. The method according to claim 1, wherein the surface of the release location is dry when the particles are released thereon.

3. The method according to claim 1, wherein the plate is a microscope slide or a growing substrate.

4. The method according to claim 1, further comprising surrounding the release location by a coating repelling the liquid medium.

5. The method according to claim 1, further comprising providing a light source under the release location.

6. The method according to claim 1, wherein the probe magnet is a vertical rod magnet and the release magnet is a vertical rod magnet.

7. The method according to claim 6, wherein a pole of the probe magnet is against an opposite pole of the release magnet.

8. An apparatus for processing magnetic particles, comprising:

a probe for collecting magnetic particles from a liquid medium, the probe comprising a hollow shield having a lower end portion with a closed lower end and a magnet movable up and down in the hollow shield, a release plate comprising a release location having a surface which is either dry, has a liquid film or a liquid drop smaller than 0.2 μl thereon, and a release magnet below the release location, wherein the apparatus is arranged to operate so that collected magnetic particles are released from the probe onto the surface of the release location, which is either dry, has a liquid film or a liquid drop smaller than 0.2 μl thereon.

9. The apparatus according to claim 8, wherein the release plate comprises a plurality of release locations.

10. The apparatus according to claim 8, wherein the liquid medium is contained in a vessel.

* * * * *